US00PP14465P39

(12) United States Plant Patent
Zaiger et al.

(10) Patent No.: US PP14,465 P3
(45) Date of Patent: Jan. 13, 2004

(54) PLUM TREE NAMED 'BIG RED'

(50) Latin Name: *Prunus salicina*
Varietal Denomination: Big Red

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 52 days.

(21) Appl. No.: 10/072,168

(22) Filed: Feb. 11, 2002

(65) Prior Publication Data

US 2003/0154528 P1 Aug. 14, 2003

(51) Int. Cl.[7] ..... A01H 5/00
(52) U.S. Cl. ..... Plt./184

(58) Field of Search ..... Plt./184

*Primary Examiner*—Kent Bell

(57) ABSTRACT

A new and distinct variety of plum tree (*Prunus salicina*). The following features of the tree and its fruit are characterized with the tree budded on 'Citation' Rootstock (U.S. Plant Pat. No. 5,112) grown on Handford sandy loam soil with Storie Index reading 95, in USDA Hardiness Zone 9, near Modesto, Calif., with standard commercial fruit growing practices, such as pruning, thinning, spraying, irrigation and fertilization. Its novelty consists of the following combination of desirable features:

1. Heavy and regular production of fruit.
2. Fruit with good flavor and eating quality.
3. Fruit with an attractive high red skin color.
4. Fruit with relative uniform large size throughout the tree.
5. Fruit with a good balance between sugar and acid, having high soluble solids, average of 16.3° Brix.

1 Drawing Sheet

Latin name of genus & species: *Prunus salicina.*
Variety denomination: 'Big Red'.

BACKGROUND OF THE VARIETY

Field of the Invention

In the field of plant genetics, we conduct an extensive and continuing plant-breeding program including the organization and asexual reproduction of orchard trees, and of which almonds, apples, apricots, cherries, peaches, plums, nectarines and interspecifics are exemplary. It was against this background of our activities that the present variety of plum tree was originated and asexually reproduced by us in our experimental orchard located near Modesto, Stanislaus County, Calif.

PRIOR VARIETIES

Among the existing varieties of plums, which are known to us, and mentioned herein are 'King David' Plum (non-patented), 'Queen Ann' Plum (non-patented), 'Casselman' Plum (non-patented), 'Friar' Plum (non-patented), 'Mariposa' Plum (U.S. Plant Pat. No. 111) and 'Ebony' Plum (U.S. Plant Pat. No. 2,049).

ORIGIN OF THE VARIETY

The new and distinct variety of plum tree (*Prunus salicina*), originated in our experimental orchard, located near Modesto, Calif., as an open pollinated seedling (pollen parent unknown) from seed collected from our proprietary parent labeled 9GF78. The maternal parent of 9GF78 originated from crosses between the following plums, 'King David' (non-patented), 'Queen Ann' (non-patented), and 'Casselman' (non-patented). The pollen parent of 9GF78 originated from crosses between the following plums, 'Friar'

(non-patented), 'Mariposa' (U.S. Plant Pat. No. 111) and 'Ebony' (U.S. Plant Pat. No. 2,049). A large group of open pollinated seeds were collected and grown on their own root system, under close and careful observation. One such seedling exhibited distinct and desirable fruit characteristics and was selected in 1991 for asexual propagation and commercialization.

ASEXUAL REPRODUCTION OF THE VARIETY

Asexual reproduction of the new plum variety was by budding to 'Citation' Rootstock (U.S. Plant Pat. No. 5112), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new plum tree is of large size, vigorous upright growth and a productive and regular bearer of very large, firm, clingstone fruit, maturing in early August at Modesto, Calif. The fruit is further characterized as having a high degree of attractive red skin color, having a good balance between sugar and acid with good flavor and eating quality. The size of the fruit is relatively uniform throughout the tree and has good storage and shipping quality. In comparison to 9GF78 the maternal parent, the new variety has better flavor and is approximately two weeks later in maturity. In comparison to the 'Friar' Plum (non-patented), the fruit of the new variety is nearly globose to slightly elongated in shape, compared to an oblate shape, has red skin color compared to blue black and is approximately one week later in maturity. In comparison to 'Casselman' Plum (non-patented), the new variety is larger in size, darker red in color and is approximately one week earlier in maturity.

PHOTOGRAPH OF THE VARIETY

The accompanying color photographic illustration shows typical specimens of the fruit and foliage of the new plum variety. The illustration shows the upper and lower surface of the leaves, an exterior and sectional view of a fruit divided in the suture plane to show flesh color, pit cavity and a stone remaining in place. The photographic illustration was taken shortly after being picked (shipping ripe) and the colors are as true as is reasonably possible in a color representation of this type.

DESCRIPTION OF THE VARIETY

The following is a detailed botanical description of the new variety of plum tree, its flowers, foliage and fruit, as based on observations of 6 year old specimens budded to 'Citation' Rootstock (U.S. Plant Pat. No. 5,112) and grown near Modesto, Calif., with color in accordance with Munsell Book of Color.

Tree:

*Size.*—Large. Pruned to 3 to 3.5 meters in height for economical harvesting of fruit.

*Vigor.*—Vigorous. Growth of 1.5 to 2 meters in height the first growing season. Varies with soil type, fertility and climatic conditions.

*Form.*—Upright, typical of normal plum growth. Usually pruned to 3 to 3.5 meters in height with vase shape.

*Branching habit.*—Upright. Crotch angle between 25 and 30 degrees when juvenile, upon maturity, the weight of the fruit tends to increase the branch angle.

*Productivity.*—Heavy production, setting 1.5 to 2 times more than the number of fruit desired, thinning and spacing of fruit necessary to produce marketable fruit.

*Density.*—Medium dense. Removal of center branches to form vase shape allows for sunlight and air movement to enhance fruit color and fruit spur growth.

*Bearer.*—Regular. Five consecutive years of adequate fruit set. No alternate bearing observed.

*Fertility.*—Self-sterile, pollenizer required.

*Hardiness.*—Hardy in all stone fruit growing areas in California. Winter chilling requirement approximately 850 hours at or below 45° F.

Trunk:

*Size.*—Large. Average circumference of 53.34 cm at 29.21 cm above ground on a 6 year old tree.

*Texture.*—Medium shaggy, increases with age.

*Color.*—10R 5/1 to 5YR 5/1, varies with age of tree.

Branches:

*Size.*—Medium. Average circumference 14.5 cm measured 1.2 m above ground.

*Texture.*—Smooth on new growth, becomes medium rough on mature growth.

*Lenticels.*—Medium number, average 46 in 25.8 square cm section. Average length 3.3 mm. Average width 1.52 mm. Color 2.5YR 7/12.

*Color.*—New growth 2.5GY 8/6 to 2.5GY 8/8. Old growth 5YR 4/4 to 5YR 4/6. Varies with age of growth.

Leaves:

*Size.*—Medium. Average length 94.2 mm. Average width 37.1 mm.

*Form.*—Oblanceolate.

*Apex.*—Acuminate.

*Base.*—Cuneate.

*Margin.*—Doubly serrate.

*Thickness.*—Medium. Average for plums.

*Surface.*—Upper surface relatively smooth, slight indentation over midrib and leaf veins, glabrous. Lower surface relatively smooth, small ridges created by midrib and pinnate venation, glabrous.

*Petiole.*—Average length 14.3 mm. Average width 1.7 mm. Grooved longitudinally. Color 5GY 6/6.

*Glands.*—Globose. Small — average length 0.8 mm, average diameter 0.5 mm. Number varies from 3 to 5, average number 3. Located on upper portion of petiole and base of leaf blade. Color 5GY 8/6.

*Color.*—Upper surface 7.5GY 3/6. Lower surface 7.5GY 6/4.

Flower buds:

*Size.*—Large. Average length 8.8 mm. Average diameter 4.9 mm.

*Form.*—Plump, conical.

*Hardiness.*—Hardy, with respect to California winters.

*Shape.*—Elongated just before opening.

*Pubescence.*—Glabrous.

*Color.*—N 9/.5.

*Pedicel.*—Medium. Average length 8.1 mm. Average width 0.8 mm. Color 5GY 6/8.

*Number of buds per spur.*—Varies from 3 to 9, average 7.

Flowers:

*Size.*—Large for plum flowers. Average height 13.2 mm. Average diameter 18.8 mm.

*Petals.*—Number 5, alternately arranged to sepals. Ovate shape. Average length 11.2 mm. Average width 9.3 mm. Color N 9/.5. Margin — entire, slightly cupped or clawed at apex.

*Sepals.*—Number 5, alternately arranged to petals. Triangular shape, both upper and lower surface glabrous. Average length 4.5 mm. Average width 2.9 mm. Color — upper surface 5GY 7/12, lower surface 5GY 6/10.

*Stamens.*—Average number per flower 36. Average filament length 8.5 mm. Filament color N 9/.5. Color of anthers 3.75Y 8/14.

*Pistil.*—Normally 1, varies from 1 to 2. Average length 10.4 mm, stigma approximately 1.7 mm higher than the anthers. Color 2.5GY 8/6. Glabrous.

*Aroma.*—Slight.

*Pollen.*—Abundant, pollen sacs full. Self-sterile, pollenizer required. Color — 3.75Y 8/14.

*Blooming period.*—Date of first bloom Feb. 28, 2001. Date of petal fall Mar. 13, 2001. Varies slightly with climatic conditions.

*Color.*—N 9/.5.

*Pedicel.*—Long, thin. Average length 9.7 mm. Average width 0.8 mm. Color 5GY 6/10.

*Number of flowers per bud.*—Usually two, varies from 1 to 3.

Fruit:

*Maturity when described.*—Firm ripe.

*Date of first picking.*—Aug. 1, 2001.

*Date of last picking.*—Aug. 6, 2001. Varies slightly with climatic conditions.

*Size.*—Very large. Average diameter axially 66.2 mm. Average transversely in suture plane 66.1 mm. Average weight 188.5 grams. Varies slightly with fertility of soil, amount of thinning and climatic conditions.

*Form.*—Nearly globose, slight enlargement to apex.

*Suture.*—Nearly smooth, extends from base to apex.

*Ventral surface.*—Relatively smooth, only slightly lipped.

*Apex.*—Slight rounded projection.

*Base.*—Retuse.

*Cavity.*—Rounded to slightly elongated in suture plane. Average depth 9.6 mm. Average breadth 12.9 mm.

Skin:

*Thickness.*—Medium. Tenacious to the flesh.

*Surface.*—Slightly waffled throughout.

*Bloom.*—Moderate amount.

*Color.*—Ground color 2.5Y 8.5/6, overspread with 2.5R 3/6 to 2.5R 3/8, very small areas of ground color exposed, giving a speckling pattern to the surface.

Stem:

*Size.*—Average length 13.3 mm. Average width 2.0 mm, enlarged at point of fruit attachment.

*Color.*—5YR 4/6.

Flesh:

*Ripens.*—Evenly.

*Texture.*—Firm, meaty.

*Fibers.*—Few, small, tender.

*Aroma.*—Slight.

*Amydgalin.*—Undetected.

*Firmness.*—Good, comparable to 'Friar' Plum (non-patented).

*Eating quality.*—Good. Good balance between acid and sugar. Average Brix 16.3°.

*Juice.*—Moderate to heavy, enhances flavor.

*Color.*—10YR 9/2 to 10YR 9/4. Pit cavity 10YR 6/6.

Stone:

*Type.*—Clingstone.

*Size.*—Medium. Average length 19.9 mm. Average width 14.1 mm. Average thickness 10.2 mm.

*Form.*—Ovate.

*Base.*—Varies from straight to pointed.

*Apex.*—Acuminate, short in length.

*Surface.*—Lightly pitted throughout. One long groove near suture on each side of stone.

*Sides.*—Unequal. One side of stone extends further from center axis.

*Ridges.*—Small, narrow ridge created by groove near suture.

*Tendency to split.*—Very slight.

*Color.*—10YR 9/2 to 10YR 8/4 when dry.

Kernal:

*Form.*—Oblong.

*Taste.*—Bitter, heavy amydgalin.

*Viability.*—Viable. Good embryo development.

*Size.*—Medium. Average length 17 mm. Average width 9.6 mm. Average breadth 6.7 mm.

*Skin color.*—10RY 6/6, when dry.

Use:

*Dessert.*—Market—Local and long distance.

Keeping quality: Good, held firm for 3 weeks in cold storage at 38° to 42° F. with no internal break down or wooliness of flesh.

Shipping quality: Good, showed minimal bruising or skin scarring in picking, packing or shipping trials.

Plant disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of plum tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of plum tree, substantially as illustrated and described, characterized by its large size, vigorous upright growth and being a productive and regular bearer of very large, clingstone fruit with good flavor and eating quality and, in comparison to the 'Friar' Plum (non-patented), the fruit is more globose in shape compared to an oblate shape, has red skin color compared to blue black and is approximately 1 week later in maturity.

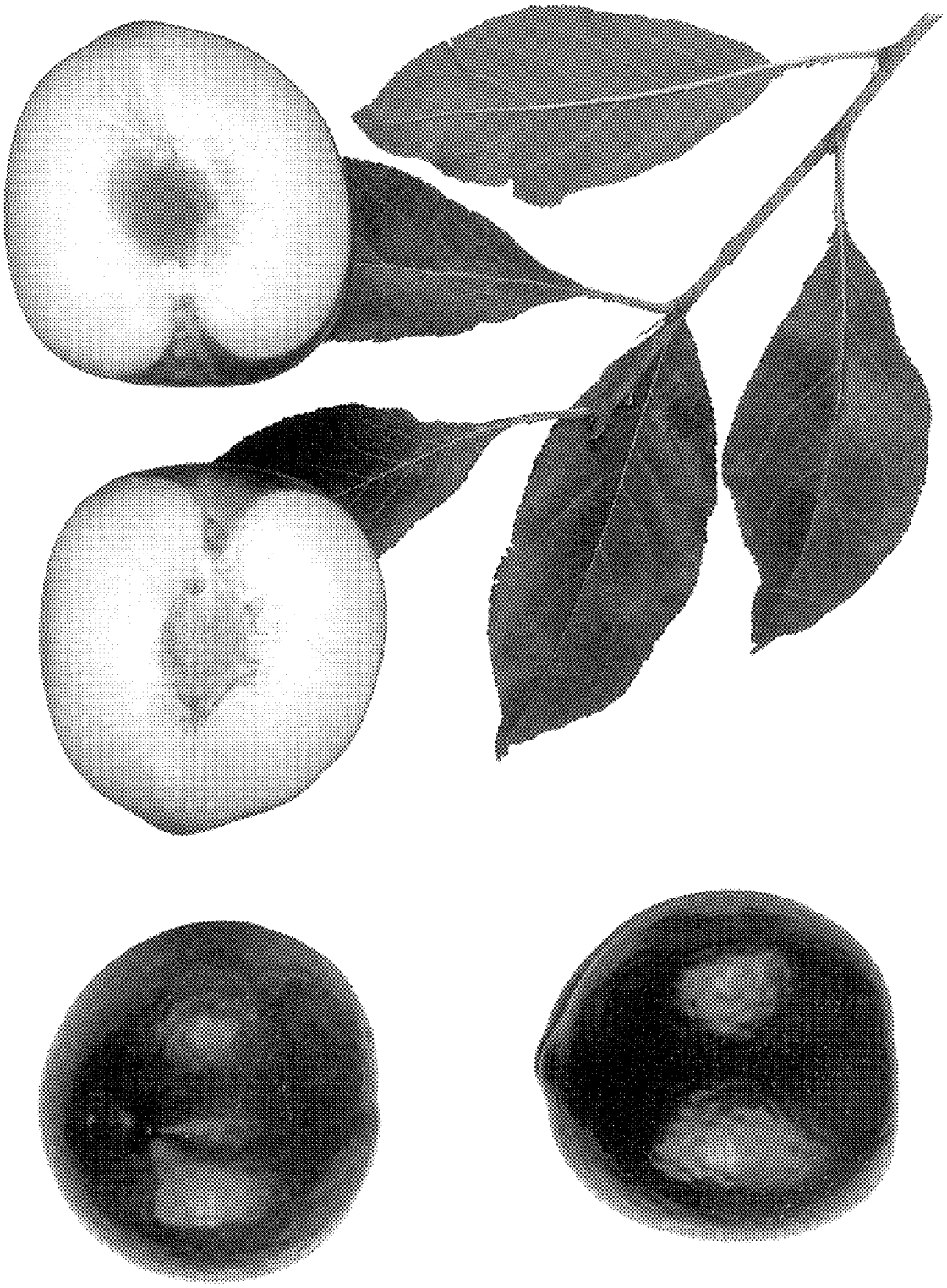

* * * * *